US012595464B1

(12) United States Patent
Sawada et al.

(10) Patent No.: US 12,595,464 B1
(45) Date of Patent: Apr. 7, 2026

(54) METHOD OF PRODUCING RETINAL PIGMENT EPITHELIAL CELL

(71) Applicants: HEALIOS K.K., Tokyo (JP); RIKEN, Wako (JP); OSAKA UNIVERSITY, Suita (JP)

(72) Inventors: Masanori Sawada, Tokyo (JP); Masayo Takahashi, Wako (JP); Kiyotoshi Sekiguchi, Suita (JP)

(73) Assignees: HELIOS K.K., Tokyo (JP); RIKEN, Wako (JP); OSAKA UNIVERSITY, Suita (JP)

( * ) Notice: Subject to any disclaimer, the term of this patent is extended or adjusted under 35 U.S.C. 154(b) by 0 days.

(21) Appl. No.: 19/062,599

(22) Filed: Feb. 25, 2025

Related U.S. Application Data

(63) Continuation of application No. 15/028,076, filed as application No. PCT/JP2014/077111 on Oct. 9, 2014, now abandoned.

(30) Foreign Application Priority Data

Oct. 9, 2013 (JP) ................................. 2013-212345

(51) Int. Cl.
$$\begin{array}{ll} C12N\ 5/079 & (2010.01) \\ A61K\ 9/00 & (2006.01) \\ A61K\ 35/30 & (2015.01) \end{array}$$

(52) U.S. Cl.
CPC .......... *C12N 5/0621* (2013.01); *A61K 9/0048* (2013.01); *A61K 35/30* (2013.01); *C12N 2501/727* (2013.01); *C12N 2506/45* (2013.01); *C12N 2509/00* (2013.01); *C12N 2533/52* (2013.01)

(58) Field of Classification Search
None
See application file for complete search history.

(56) References Cited

U.S. PATENT DOCUMENTS

| | | |
|---|---|---|
| 2008/0044901 A1 | 2/2008 | Sasai et al. |
| 2010/0105137 A1 | 4/2010 | Takahashi et al. |
| 2011/0027333 A1 | 2/2011 | Idelson et al. |
| 2012/0220031 A1 | 8/2012 | Sekiguchi et al. |
| 2013/0196369 A1 | 8/2013 | Hikita et al. |
| 2013/0224156 A1 | 8/2013 | Takahashi et al. |
| 2014/0057281 A1 | 2/2014 | Takahashi et al. |
| 2015/0175964 A1 | 6/2015 | Clegg et al. |
| 2016/0244721 A1 | 8/2016 | Sawada et al. |

FOREIGN PATENT DOCUMENTS

| | | |
|---|---|---|
| SG | 192878 A1 | 9/2013 |
| WO | WO 2005/123902 A1 | 12/2005 |
| WO | WO 2008/129554 A1 | 10/2008 |
| WO | WO 2011/043405 A1 | 4/2011 |
| WO | WO 2012/115244 A1 | 8/2012 |

OTHER PUBLICATIONS

Aumailley et al., "A simplified laminin nomenclature," *Matrix Biol.*, 24(5): 326-332 (2005).
Aumailley, "The laminin family," *Cell Adh. Migr.*, 7(1): 48-55 (2013).
Bayramov et al., "Novel functions of Noggin proteins: inhibition of Activin/Nodal and Wnt signaling," *Development*, 138(24): 5345-5356 (2011).
Borooah et al., "Using human induced pluripotent stem cells to treat retinal disease," *Progress in Retinal and Eye Research*, 37: 163-181 (2013).
Buchholz et al., "Derivation of Functional Retinal Pigmented Epithelium from Induced Pluripotent Stem Cells," *Stem Cells*, 27(10): 2427-2434 (2009).
Chambers et al., "Highly efficient neural conversion of human ES and iPS cells by dual inhibition of SMAD signaling," *Nat. Biotech.*, 27(3): 275-280 (2009).
Drago et al., "Laminin through its long arm E8 fragment promotes the proliferation and differentiation of murine neuroepithelial cells in vitro," *Exp. Cell Res.*, 192(1): 256-265 (1991).
Durbeej et al., "Dystroglycan binding to laminin α1LG4 module influences epithelial morphogenesis of salivary gland and lung in vitro," *Differentiation*, 69(2-3): 121-134 (2001).
Galvin et al., "Dystroglycan modulates the ability of insulin-like growth factor-1 to promote oligodendrocyte differentiation," *J. Neurosci. Res.*, 88(15): 3295-3307 (2010).
Idelson et al., "Differentiation of Human Pluripotent Stem Cells into Retinal Cells," in *Stem Cells and Cancer Stem Cells*, vol. 6 (Therapeutic Applications in Disease and Injury), M. Hayat (ed.), Chapter 9, pp. 87-99 (2012).
Kuroda et al., "Highly Sensitive In Vitro Methods for Detection of Residual Undifferentiated Cells in Retinal Pigment Epithelium Cells Derived from Human iPS Cells," *PLoS One*, 7(5): e37342 (2012).

(Continued)

*Primary Examiner* — Evelyn Y Pyla

(74) *Attorney, Agent, or Firm* — Leydig, Voit & Mayer, Ltd.

(57) ABSTRACT

Provided are a production method of retinal pigment epithelial (RPE) cells that improves differentiation induction efficiency of pluripotent stem cells into RPE cells, and can provide highly pure RPE cells by a simple and easy operation in a short period, a culture method of RPE cells that can stably grow and culture a cell, a toxicity/efficacy evaluation method using RPE cells useful for transplantation therapy, and a therapeutic drug for a retinal disease. The invention relates to a production method of RPE cells, comprising adhesion culture of human pluripotent stem cells using a culture substrate coated with a laminin-E8 fragment, a culture method of RPE cells, comprising adhesion culture of RPE cells using a culture substrate coated with a laminin-E8 fragment, a toxicity or efficacy evaluation method using RPE cells obtained by producing or culturing by the method, and a therapeutic drug for a retinal disease, containing the RPE cells.

12 Claims, 4 Drawing Sheets

Specification includes a Sequence Listing.

(56) References Cited

OTHER PUBLICATIONS

Miyazaki et al., "Laminin E8 fragments support efficient adhesion and expansion of dissociated human pluripotent stem cells," *Nature Communications*, 3: 1236, Erratum, and Supplementary Information (2012).

Muschler et al., "Division of Labor among the α6β4 Integrin, β1 Integrins, and an E3 Laminin Receptor to Signal Morphogenesis and β-Casein Expression in Mammary Epithelial Cells," *Mol. Biol. Cell*, 10(9): 2817-2828 (1999).

Osakada et al., "In vitro differentiation of retinal cells from human pluripotent stem cells by small-molecule induction," *J. Cell Sci.*, 122(17): 3169-3179 (2009).

Peng et al., "Tight Junctions of RPE Derived from Human Embryonic Stem Cells," *Visionary Genomics*, program/poster 2237/A403 (May 2, 2011).

Rodin et al., "Long-term self-renewal of human pluripotent stem cells on human recombinant laminin-511," *Nature Biotechnology*, 28(6): 611-615 (2010).

Rowland et al., "Differentiation of human pluripotent stem cells to retinal pigmented epithelium in defined conditions using purified extracellular matrix proteins," *Journal of Tissue Engineering and Regenerative Medicine*, 7: 642-653 (2013).

Schéele et al., "Laminin a1 globular domains 4-5 induce fetal development but are not vital for embryonic basement membrane assembly," *Proc. Natl. Acad. Sci. U.S.A.*, 102(5): 1502-1506 (2005).

Sekiguchi et al., "Development of Pluripotent Stem Cell Feeder-Free Culture Substrate," *Clinical Evaluation*, 41(1): 124-127 (2013).

Shiraki et al., "Efficient Differentiation of Embryonic Stem Cells into Hepatic Cells In Vitro Using a Feeder-Free Basement Membrane Substratum," *PLoS One*, 6(8): e24228 (2011).

Taniguchi et al., "The C-terminal Region of Laminin β Chains Modulates the Inegrin Binding Affinities of Laminins," *The Journal of Biological Chemistry*, 284(12): 7820-7831 (2009).

Zhu et al., "Three-Dimensional Neuroepithelial Culture from Human Embryonic Stem Cells and Its Use for Quantitative Conversion to Retinal Pigment Epithelium," *PLoS One*, 8(1): e54552 (2013).

European Patent Office, Supplementary European Search Report in European Patent Application No. 14851809.5 (Jun. 28, 2017).

European Patent Office, Main Request Claims before the Opposition Division of the European Patent Office in European Patent Application No. 14852053.9 (Mar. 4, 2024).

European Patent Office, Interlocutory Decision of the Opposition Division of the European Patent Office in European Patent Application No. 14852053.9 (Mar. 20, 2024).

European Patent Office, Minutes of the Oral Proceedings before the Opposition Division of the European Patent Office in European Patent Application No. 14852053.9 (Mar. 20, 2024).

Japanese Patent Office, International Search Report in International Patent Application No. PCT/JP2014/077111 (Jan. 13, 2015).

The International Bureau of WIPO, International Preliminary Report on Patentability and Written Opinion of the International Searching Authority in International Patent Application No. PCT/JP2014/077111 (Apr. 12, 2016).

U.S. Appl. No. 15/028,076, filed Apr. 8, 2016, Pending.

U.S. Appl. No. 15/028,158, filed Apr. 8, 2016, Patented.

Laminin-511        E8 fragment expression of RPE-related gene configuration of each lane

| lane | gene name | sample |
|------|-----------|--------|
| 1 | marker | 100bp DNA ladder |
| 2 | BEST1 | 1120C7 |
| 3 | | 201B7 |
| 4 | | negative control (water) |
| 5 | | positive control (Lonza Human RPE) |
| 6 | Blank | water |
| 7 | RPE65 | 1120C7 |
| 8 | | 201B7 |
| 9 | | negative control (water) |
| 10 | | positive control (Lonza Human RPE) |
| 11 | Blank | water |
| 12 | Blank | water | laminin 511-E8 (start of differentiation induction October 11, 2013)

| next day of seeding (10/12) | day 2(10/13) | day 3 (10/14) |
| --- | --- | --- |

Matrigel (start of differentiation induction October 11, 2013)

| next day of seeding (10/12) | day 2(10/13) | day 3 (10/14) |
| --- | --- | --- | laminin 511 full-length (start of differentiation induction October 11, 2013)

| next day of seeding (10/12) | day 2(10/13) | day 3 (10/14) |
| --- | --- | --- | laminin 511-E8

Matrigel laminin 511-full-length

```
                          SEQUENCE LISTING

Sequence total quantity: 8
SEQ ID NO: 1              moltype = DNA   length = 20
FEATURE                   Location/Qualifiers
misc_feature              1..20
                          note = Synthetic Oligonucleotide
source                    1..20
                          mol_type = other DNA
                          organism = synthetic construct
SEQUENCE: 1
tccccaatac aactgccact                                          20

SEQ ID NO: 2              moltype = DNA   length = 20
FEATURE                   Location/Qualifiers
misc_feature              1..20
                          note = Synthetic Oligonucleotide
source                    1..20
                          mol_type = other DNA
                          organism = synthetic construct
SEQUENCE: 2
ccttggcatt cagaatcagg                                          20

SEQ ID NO: 3              moltype = DNA   length = 20
FEATURE                   Location/Qualifiers
misc_feature              1..20
                          note = Synthetic Oligonucleotide
source                    1..20
                          mol_type = other DNA
                          organism = synthetic construct
SEQUENCE: 3
gagggtgcaa gagaaggaca                                          20

SEQ ID NO: 4              moltype = DNA   length = 20
FEATURE                   Location/Qualifiers
misc_feature              1..20
                          note = Synthetic Oligonucleotide
source                    1..20
                          mol_type = other DNA
                          organism = synthetic construct
SEQUENCE: 4
tgcagaagcc attgatttga                                          20

SEQ ID NO: 5              moltype = DNA   length = 20
FEATURE                   Location/Qualifiers
misc_feature              1..20
                          note = Synthetic Oligonucleotide
source                    1..20
                          mol_type = other DNA
                          organism = synthetic construct
SEQUENCE: 5
tccttggcca tcagaaaaag                                          20

SEQ ID NO: 6              moltype = DNA   length = 20
FEATURE                   Location/Qualifiers
misc_feature              1..20
                          note = Synthetic Oligonucleotide
```

-continued

```
source                  1..20
                        mol_type = other DNA
                        organism = synthetic construct
SEQUENCE: 6
catttgggtg gctgaagtct                                        20

SEQ ID NO: 7            moltype = DNA   length = 19
FEATURE                 Location/Qualifiers
misc_feature            1..19
                        note = Synthetic Oligonucleotide
source                  1..19
                        mol_type = other DNA
                        organism = synthetic construct
SEQUENCE: 7
tagaaccatc agcgccgtc                                         19

SEQ ID NO: 8            moltype = DNA   length = 21
FEATURE                 Location/Qualifiers
misc_feature            1..21
                        note = Synthetic Oligonucleotide
source                  1..21
                        mol_type = other DNA
                        organism = synthetic construct
SEQUENCE: 8
tgagtgtagt gtgtatgttg g                                      21
```

METHOD OF PRODUCING RETINAL PIGMENT EPITHELIAL CELL

CROSS-REFERENCE TO RELATED APPLICATIONS

This patent application is a continuation of copending U.S. patent application Ser. No. 15/028,076, filed on Apr. 8, 2016, which is the U.S. national phase of International Patent Application No. PCT/JP2014/077111, filed Oct. 9, 2014, which claims the benefit of Japanese Patent Application No. 2013-212345, filed on Oct. 9, 2013.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: One 11, 165 Byte Extensible Markup Language (XML) file named "772706_Sequence_Listing.xml," dated Feb. 25, 2025.

TECHNICAL FIELD

The present invention relates to a method of efficiently producing retinal pigment epithelial (RPE) cells from human pluripotent stem cells, a method of stably culturing retinal pigment epithelial cells, and the like.

BACKGROUND ART

As a method for producing retinal pigment epithelial cells from pluripotent stem cells, a method called SFEB method including culturing ES cells as a floating aggregate in a serum-free medium (patent document 1 etc.), a method including inducing differentiation of pluripotent stem cells in the presence of a differentiation-inducing factor on a culture substrate coated with a weakly cell adhesive coating agent and the like (non-patent document 1 etc.) are known. However, due to the low differentiation induction efficiency, these methods require plural steps combining adhesion culture and floating culture to obtain a highly concentrated cell population of retinal pigment epithelial cells, and have problems such as the required presence of a purification step with a high workload and a long time, which includes selectively picking up a colony of pigment cells under an optical microscope. Moreover, these methods have a problem of easy cell loss during passage culture. Therefore, a method capable of stably affording highly pure retinal pigment epithelial cells by a simple and easy method has been demanded.

For maintenance culture of human pluripotent stem cells, a method using an extracellular matrix instead of a feeder cell has been widely used. Among others, laminin is being preferably used and, for example, non-patent document 2 reports successful maintenance culture of human ES cell on laminin-511 for a long term. As for E8 fragment known as an altered laminin having an improved cell adhesion activity, for example, patent document 2 and non-patent document 3 disclose culture methods of human pluripotent stem cells, which use E8 fragment of human laminin-α5β1γ1 (laminin-511E8, hereinafter indicated in the same manner) and human laminin-322E8. Non-patent document 4 describes that laminin-511E8 maintains binding activity to α6β1 integrin, which is of the same level as that of full-length laminin-511, and patent document 2 describes that, by using said laminin- 511E8, pluripotent stem cells can be stably immobilized on a culture dish, as a result of which the cells, while maintaining differentiation pluripotency, can be subjected to maintenance culture. However, no report has documented utilization of such E8 fragment of laminin for other than culture of pluripotent stem cells, for example, differentiation induction of pluripotent stem cells and the like.

On the other hand, as a method of inducing differentiation of human pluripotent stem cells into retinal pigment epithelial cells in the absence of a feeder cell, a method using laminin is known. For example, non-patent document 5 describes that the differentiation induction efficiency into retinal pigment epithelial cells markedly increased by adhesion culture of pluripotent stem cells on laminin-111 and MATRIGEL. However, no report has documented use of the E8 fragment of laminin for the induction of differentiation of pluripotent stem cell into retinal pigment epithelial cell.

DOCUMENT LIST

Patent Documents patent document 1: WO 2005/123902
patent document 2: WO 2011/043405

Non-Patent Documents non-patent document 1: PLOS One. 2012; 7(5): e37342.
non-patent document 2: Nature Biotech. June 2010; 28(6): 611-5
non-patent document 3: Nat. Commun. 3:1236 doi: 10.1038/ncomms2231
non-patent document 4: J Biol Chem. 284:7820-7831, 2009
non-patent document 5: J. Tissue Eng Regen Med 2013; 7:642-653

SUMMARY OF THE INVENTION

Problems to be Solved by the Invention

An object of the present invention is to provide a production method of retinal pigment epithelial cell that improves differentiation induction efficiency of pluripotent stem cell into retinal pigment epithelial cell, and can provide highly pure retinal pigment epithelial cell by a simple and easy operation in a short period, a culture method of retinal pigment epithelial cell that can stably grow and culture a cell, a toxicity/efficacy evaluation method using a retinal pigment epithelial cell useful for transplantation therapy, and a therapeutic drug for a retinal disease.

Means of Solving the Problems

The present inventors have conducted intensive studies in an attempt to achieve the above-mentioned objects and found that, when human pluripotent stem cells are cultured on a culture substrate coated with laminin-E8, the seeded pluripotent stem cells rapidly adhere to the culture substrate, a large amount of pigment cell is generated from early stages, the yield of retinal pigment epithelial cells can be markedly improved, cells are not easily lost during medium exchange, the purification step can be simplified, and a highly pure cell population can be obtained in a short period. As a result, the operability and economic efficiency, which are the problems in inducing differentiation of pluripotent stem cells into retinal pigment epithelial cells, can be markedly improved, and the retinal pigment epithelial cells of interest can be produced stably and efficiently, which resulted in the completion of the present invention.

That is, the present invention relates to the following.

[1] A production method of retinal pigment epithelial cells, comprising a step of adhesion culture of human pluripotent stem cells on a culture substrate coated with a laminin-E8 fragment.

[2] The method of [1], wherein the laminin-E8 fragment is laminin-511E8 fragment.

[3] The method of [1] or [2], wherein the step of adhesion culture is performed in the presence of a differentiation-inducing factor.

[4] The method of any of [1]-[3], wherein the human pluripotent stem cells are human iPS cells.

[5] A retinal pigment epithelial cell produced by adhesion culture of human pluripotent stem cells on a culture substrate coated with a laminin-E8 fragment.

[6] A retinal pigment epithelial cell sheet produced by adhesion culture of human pluripotent stem cells on a culture substrate coated with a laminin-E8 fragment.

[7] An amplification method of retinal pigment epithelial cells, comprising a step of adhesion culture of retinal pigment epithelial cells on a culture substrate coated with a laminin-E8 fragment.

[8] A purification method of retinal pigment epithelial cells, comprising a step of adhesion culture of retinal pigment epithelial cells on a culture substrate coated with a laminin-E8 fragment.

[9] A therapeutic drug for a retinal disease, comprising retinal pigment epithelial cells produced by the method of any of [1]-[4], or retinal pigment epithelial cells cultured by the method of [7].

Effect of the Invention

According to the present invention, retinal pigment epithelial cells can be produced in a high yield from pluripotent stem cells. In addition, differentiation induction efficiency is improved, and a cell population containing retinal pigment epithelial cells at a high concentration can be obtained, and highly pure retinal pigment epithelial cells can be produced by a simple and easy purification operation. According to the present invention, moreover, since retinal pigment epithelial cells can be stably adhered, the cells are not easily lost during medium exchange, and can be stably passaged.

DESCRIPTION OF EMBODIMENTS

Figure 1:
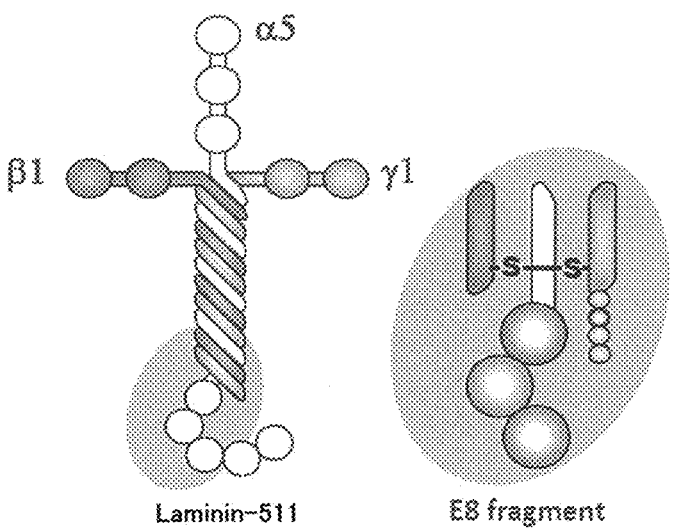
FIG. 1 is a schematic showing of the structure of laminin-E8.

1. Production Method of Retinal Pigment Epithelial Cells

The present invention is a production method of retinal pigment epithelial cells, comprising a step of adhesion culture of human pluripotent stem cells by using a culture substrate coated with a laminin-E8 fragment (hereinafter to be referred to as "the production method of the present invention").

The "pluripotent stem cell" in the present invention means a stem cell having self-replication competence and differentiation pluripotency, and is not particularly limited. For example, embryonic stem cells (ES cell), induced pluripotent stem cells (iPS cell) and the like are widely utilized. Preferably, human ES cells or human iPS cells are utilized and, more preferably, human iPS cells are utilized.

The "iPS cell" in the present invention means a cell that artificially acquired self-replication competence and differentiation pluripotency by contacting a nuclear reprogramming factor with somatic cells (e.g., fibroblast, skin cell, lymphocyte etc.). The production method of iPS cells in the present invention is not particularly limited.

The "retinal pigment epithelial cell" in the present invention refers to an epithelial cell constituting the retinal pigment epithelium, and a progenitor cell thereof. Whether a retinal pigment epithelial cell or not can be confirmed by, for example, expression of cell markers (RPE65, CRALBP, MERTK, BEST1 etc.), cell forms (intracellular melanin dye deposition, polygonal and flat cell form, formation of polygonal actin bundle etc.) and the like. The progenitor cell of retinal pigment epithelial cell means a cell directed to be induced to differentiate into retinal cell, and whether a progenitor cell or not can be confirmed by expression of cell markers (Mitf, Pax6, Rx, Crx etc.) and the like. Functional evaluation of retinal pigment epithelial cell can be confirmed using, for example, secretability, phagocytic capacity and the like of cytokine (VEGF, PEDF etc.) as an index. These functional evaluation and confirmation operations can be performed by those of ordinary skill in the art by setting appropriate conditions.

The "laminin" in the present invention is a heterotrimer molecule consisting of α, β, γ chains, and is an extracellular matrix protein containing isoforms having different subunit chain compositions. Specifically, laminin has about 15 kinds of isoforms including heterotrimers of combinations of 5 kinds of α chain, 4 kinds of β chain and 3 kinds of γ chain. The number of each of α chain (α1-α5), β chain (β1-β4) and γ chain (γ1-γ3) is combined to determine the name of laminin. For example, a laminin composed of a combination of α1 chain, β1 chain, γ1 chain is named laminin-111, a laminin composed of a combination of α5 chain, β1 chain, γ1 chain is named laminin-511, and a laminin composed of a combination of α5 chain, β2 chain, γ1 chain is named laminin-521. As laminin, for example, a laminin derived from a mammal can be used. Examples of the mammal include mouse, rat, guinea pig, hamster, rabbit, cat, dog, sheep, swine, bovine, horse, goat, monkey and human. Human laminin is preferably used when retinal pigment epithelial cells are produced for the purpose of transplanting to human, and the like. At the present stage, human laminin is known to include 15 kinds of isoforms.

Laminin-E8 fragment was originally one of the fragments obtained by digesting mouse laminin-111 with elastase, and identified as a fragment having strong cell adhesion activity (EMBO J., 3:1463-1468, 1984., J. Cell Biol., 105:589-598, 1987.). When digested with elastase, the presence of a fragment corresponding to the E8 fragment of mouse laminin-111 is assumed in laminin other than mouse laminin-111. However, separation and identification of E8 fragment by digestion of laminin other than mouse laminin-111 with elastase has not been reported heretofore. Therefore, laminin-E8 fragment to be used in the present invention is not required to be an elastase digestion product of each laminin, but may be a recombinant as long as it is a fragment of laminin having a cell adhesion activity similar to that of each corresponding laminin and having a structure corresponding to that of E8 fragment digested with elastase. That is, the "laminin-E8 fragment (hereinafter sometimes to be indicated as "laminin-E8")" in the present invention refers to a molecule constituting a heterotrimer in each C-terminal region of α chain, β chain and γ chain, maintaining a binding activity to integrin, as well as maintaining a cell adhesion activity. Laminin-E8 shows integrin binding specificity that varies for each laminin isoform, and can exert a strong adhesion activity to a cell that expresses the corresponding integrin.

When concretely explained, laminin-E8 in the present invention is a laminin fragment having, (1) functionally, cell adhesion activity at least equivalent to that of full-length laminin, and at least equivalent integrin binding activity, and (2) structurally, a structure corresponding to that of mouse laminin-E8, specifically, a structure corresponding to a region from coiled-coil C-terminal region of laminin trimer to 1st-3rd of G domain. It is explained in more detail in the following from the (1) functional aspect and (2) structural aspect.

(1) Function of Laminin-E8

Examples of the laminin-E8 in the present invention include a molecule showing binding specificity to at least one of the integrins expressed on the surface of human pluripotent stem cell and/or human retinal pigment epithelial cell, preferably, a molecule showing binding specificity to an integrin expressed on the surface of both human pluripotent stem cells and human retinal pigment epithelial cells, and an integrin expressed on the surface of human retinal pigment epithelial cells are preferably used. Examples of the integrin expressed on the surface of human pluripotent stem cell include α6β1 integrin and the like, and examples of the integrin expressed on the surface of human retinal pigment epithelial cell include α6β1 integrin, α3β1 integrin, α7β1 integrin and the like.

Laminin-E8 in the present invention shows binding specificity to integrin at least equivalent to each laminin. Laminin-E8 showing particularly strong affinity to integrin is preferably used. "Laminin-E8 showing particularly strong affinity to integrin" is one showing a significantly low dissociation constant as measured by a known method and, for example, the dissociation constant measured by, for example, the method shown in Table 1 of The Journal of Biological Chemistry (2009) 284, pp. 7820-7831 is not more than 10 nM.

As laminin-E8 in the present invention, one having a strong cell adhesion activity is preferably used. The "laminin-E8 having a strong cell adhesion activity" is one showing a significantly strong adhesion activity in a cell adhesion test with measurement by a known method and shows an adherent cell number of not less than 400 cells/mm$^2$ at a coating concentration of laminin-E8 of not more than 10 nM when, for example, the cell adhesion assay described in The Journal of Biological Chemistry (2007) 282, pp. 11144-11154 is performed.

In the present invention, as laminin-E8, one showing binding specificity to α6β1 integrin, capable of stably adhering pluripotent stem cells in the initial stage of differentiation induction, and capable of stably adhering retinal pigment epithelial cells in the latter stage of differentiation induction or progenitor cells thereof is preferably used. From such aspect, particularly, laminin-511 E8 is highly preferable among laminin-E8, since it has binding specificity to α3β1 integrin and α7β1 integrin in addition to α6β1 integrin, and can contribute to the improvement of differentiation induction efficiency of pluripotent stem cells into retinal pigment epithelial cells, or stabilization of maintenance culture of retinal pigment epithelial cells, by improving the adhesion activity to retinal pigment epithelial cells.

(2) Structure of Laminin-E8

The laminin-E8 in the present invention is, as mentioned above or shown in FIG. 1, a laminin fragment structurally corresponding to a fragment having a cell adhesion activity (E8 fragment) in an elastase digestion product of mouse laminin-111. That is, it maintains a part of domain II (triple-stranded coiled-coil domain) of full-length laminin (E8 fragment depicted in FIG. 1 does not show such manner but actually maintains a coiled-coil structure), and forms a short coiled-coil structure on the N terminal side of E8 with a corresponding fragment of β chain and a corresponding fragment of γ chain. On the C-terminal side of E8, the G1-G3 domain structure of α chain is maintained. The β chain and γ chain are bonded to each other by forming a disulfide bond via a cysteine residue on each C-terminal side.

As described above, laminin-E8 in the present invention may be an enzyme-treated product obtained by treating natural laminin with elastase, or a recombinant produced by gene recombination. When the laminin-E8 in the present invention is a recombinant, a tag may be bonded to the N terminal for the purpose of purification and the like as long as the binding activity of the corresponding full-length (natural) laminin to integrin is maintained, and the cell adhesiveness is not impaired. Such tag is not particularly limited and, for example, His tag, Flag tag, HA tag and the like can be mentioned. Also, the sequence of the linker region between the tag and laminin-E8 is not particularly limited as long as the binding activity of the corresponding full-length (natural) laminin to integrin is maintained, and cell adhesiveness is not impaired.

In the laminin-E8 in the present invention, a part of the amino acid sequence may be deleted, added, or substituted as long as the binding activity of the corresponding laminin to integrin is maintained, and the cell adhesiveness thereof is not impaired.

While E8 fragment generally lacks two G domains (G4 and G5) on the α chain C-terminal side, the G4, G5 domains may be partly or entirely contained in the laminin-E8 in the present invention as long as the binding activity of the corresponding full-length (natural) laminin to integrin is maintained, and cell adhesiveness thereof is not impaired. For example, the G4, G5 domains may be partly or entirely contained in the laminin-511 E8 as long as the binding activity to integrin α6β1 of the equivalent level as laminin-511 is maintained, and the cell adhesion activity is not impaired.

Like full-length laminin, β chain and γ chain of laminin-E8 are bonded via cysteine on the C-terminal side of the coiled-coil part. Since the cysteine influences the integrin binding activity, it is desirably not substituted or deleted. Furthermore, since the C-terminal side amino acid following said cysteine in the γ chain also influences the integrin binding activity, it is desirably at least not deleted (J Biol Chem. 2007 Apr. 13; 282(15):11144-54.).

Specific examples of such laminin-E8 include rhLM511E8 produced in Example (3) of WO 2011/043405. Said laminin-511E8 can be preferably utilized as the laminin-E8 in the present invention.

The "culture substrate" to be used in the present invention can be produced by coating a surface of an incubator with the laminin-E8 in the present invention. As used herein, "coating" a surface of an incubator means adsorption of laminin-E8 to the surface of the incubator by some interaction between laminin-E8 and the incubator surface, where the orientation of the laminin-E8 does not pose a particular problem in affording the effect of the present invention. The incubator is not particularly limited as long as it can be used for cell culture and, for example, dish (also referred to as culture dish), petri dish and plate (microtiter plate, microplate, deep well plate etc. of 6 well, 24 well, 48 well, 96 well, 384 well, 9600 well and the like), flask, chamber slide, tube, Cell Factory, roller bottle, spinner flask, hollow fiber, microcarrier, bead and the like can be mentioned. The culture substrate in the present invention may be applied with an appropriate surface treatment as long as the cell adhesion property by laminin-E8 is not impaired.

The "adhesion culture" in the present invention means culture in a state where the cells of interest are adhered to the bottom of the incubator via laminin-E8, and do not float in the culture medium even when the incubator is gently shaken during culture. Since laminin-E8 to be used in the present invention shows extremely superior cell adhesiveness, the cells after cell seeding are preferably uniformly dispersed by a method including rapidly trembling the incubator and the like. The cells of interest may be subjected to floating culture in an incubator containing laminin-E8 before and after the adhesion culture, as long as the object of the present invention can be achieved.

The medium is constituted of a basal medium, a serum and/or a serum replacement, and other components. As the basal medium, one or plural kinds of synthetic media generally used for culturing mammalian cells can be used in combination and, for example, commercially available products such as DMEM, GMEM and the like can be obtained.

As the serum, a serum derived from a mammal such as bovine, human and the like can be used. The serum replacement is a low-protein replacement that replaces serum such as FBS and the like used for the cell culture, and commercially available products such as Knockout Serum Replacement (KSR), Chemically-defined Lipid concentrated (manufactured by Gibco), Glutamax (manufactured by Gibco) and the like, as well as N2, B27 and the like which are serum replacements for nerve cell culture can be obtained. In the present invention, a serum replacement is preferable, and KSR is particularly preferable from the aspect of quality management of the cell of interest.

The concentration of serum or serum replacement can be appropriately set within the range of, for example, 0.5-30% (v/v). The concentration may be constant, or gradually changed. For example, the concentration may be lowered in stages at intervals of about 1-3 days (preferably 2 days). For example, serum or serum replacement can be added at 3 stages of concentration of 20%, 15% and 10%.
RhoRhoRho RhoRhoRho As other component constituting the medium, a kinase inhibitor such as Y-27632 and the like can be used to suppress cell death of human pluripotent stem cells dispersed in a culture medium. A kinase inhibitor may be added in the period of a part or the whole period of the differentiation induction step. For example, unnecessary cells that did not differentiate into the cell of interest can be removed by cell death by using a medium free of a kinase inhibitor in the latter period of the differentiation induction step.

The medium can contain other components generally used for culturing mammalian cells, besides those mentioned above.

The concentration of human pluripotent stem cells to be used in the production method of the present invention is not particularly limited as long as pluripotent stem cells can be uniformly seeded, and adhesion culture is possible. For example, when a 10 cm dish is used, it is $1\times10^5$-$1\times10^8$ cells, preferably $2\times10^6$-$5\times10^7$ cells, more preferably $5\times10^5$-$9\times10^6$ cells, per 1 dish.

The adhesion culture in the production method of the present invention can also be performed in the presence of a differentiation-inducing factor. As the differentiation-inducing factor, a factor known as a factor promoting differentiation induction into the cell of interest can be utilized. Since the production method of the present invention includes differentiation induction into retinal pigment epithelial cells, a differentiation-inducing factor into retinal pigment epithelial cells is desirably used. Examples of the differentiation-inducing factor into retinal pigment epithelial cells include Nodal signal inhibitor, Wnt signal inhibitor, Sonic hedgehog signal inhibitor, and Activin signal promoter and the like.

The Nodal signal inhibitor is not particularly limited as long as it can suppress signal transduction mediated by Nodal, and protein, nucleic acid, low-molecular-weight compound and the like can be used. Examples of the Nodal signal inhibitor include protein, peptide or nucleic acid such as Lefty-A, soluble Nodal receptor, anti-Nodal antibody, Nodal receptor inhibitor and the like; low-molecular-weight compound such as SB-431542 and the like, and the like. Particularly, a low-molecular-weight compound such as SB-431542 and the like which is easily available and shows less difference between lots is preferable.

The Wnt signal inhibitor is not particularly limited as long as it can suppress signal transduction mediated by Wnt, and protein, nucleic acid, low-molecular-weight compound and the like can be used. Examples of the Wnt signal inhibitor include protein, peptide or nucleic acid such as Dkk1, Cerberus protein, Wnt receptor inhibitor, soluble Wnt receptor, Wnt antibody, casein kinase inhibitor, dominant negative Wnt protein and the like; and low-molecular-weight compound such as CKI-7 (N-(2-aminoethyl)-5-chloro-isoquinoline-8-sulfonamide), D4476(4-{4-(2,3-dihydrobenzo[1,4]dioxin-6-yl)-5-pyridin-2-yl-1H-imidazol-2-yl}benzamide), IWR-1-endo (IWR1e), IWP-2 and the like. Particularly, a low-molecular-weight compound which is easily available and shows less difference between lots is preferable. Among others, a low-molecular-weight compound having an activity to selectively inhibit casein kinase I is preferable and, for example, CKI-7, D4476 and the like can be utilized.

Examples of the Activin signal promoter include protein belonging to the Activin family, Activin receptor, Activin receptor agonist and the like.

The concentration of these differentiation-inducing factors can be appropriately selected according to the kind of the differentiation-inducing factor. Specifically, when SB-431542 is used as a Nodal signal inhibitor, the concentration is, for example, 0.01-50 μM, preferably 0.1-10 μM, more preferably 5 μM; when CKI-7 is used as a Wnt signal inhibitor, it is added at the concentration of 0.01-30 μM, preferably 0.1-30 μM, more preferably 3 μM.

In the production method of the present invention, a combination of a Nodal signal inhibitor (e.g., SB-431542) and a Wnt signal inhibitor (e.g., CKI-7) is preferably used as a differentiation-inducing factor.

Culture according to the aforementioned method induces differentiation of pluripotent stem cells into retinal pigment epithelial cells, whereby retinal pigment epithelial cells can be generated generally on day 25-45 from the seeding of pluripotent stem cells. Generation of retinal pigment epithelial cell can be confirmed according to the aforementioned method. When generation of retinal pigment epithelial cells is confirmed, the medium is exchanged with a maintenance medium for retinal pigment epithelial cells and, for example, the cells are preferably further cultured for 5-10 days while exchanging the total amount of medium at a frequency of not less than once in 3 days. As a result, a melanin dye deposition cell population and a polygonal flat cell population adhered to the basal lamina can be observed more clearly.

As the maintenance medium for retinal pigment epithelial cells, for example, those described in IOVS, March 2004, Vol. 45, No. 3, Masatoshi Haruta, et. al., IOVS, November 2011, Vol. 52, No. 12, Okamoto and Takahashi, J. Cell Science 122 (17), Fumitaka Osakada, et. al., IOVS, February 2008, Vol. 49, No. 2, Gamm, et. al. can be used, which are constituted of a basal medium, a serum and/or a serum replacement, and other components. As the basal medium, one or plural kinds of synthetic media generally used for culturing mammalian cells can be used in combination and, for example, commercially available products such as DMEM, GMEM and the like can be obtained.

As the serum, a serum derived from a mammal such as bovine, human, swine and the like can be used. The serum replacement is a low-protein replacement that replaces serum such as FBS and the like used for the cell culture, and commercially available products such as Knockout Serum Replacement (KSR), Chemically-defined Lipid concentrated (manufactured by Gibco), Glutamax (manufactured by Gibco) and the like, as well as N2, B27 and the like which are serum replacements for nerve cell culture can be obtained. In the present invention, a serum replacement is preferable, and B27 is particularly preferable from the aspect of quality management of the cell of interest.

Examples of other components include L-glutamine, penicillin sodium, sulfuric acid streptomycin and the like.

The production method of the present invention may further contain a step of purifying retinal pigment epithelial cells by a concentration operation. Since the production method of the present invention markedly improves the differentiation induction efficiency, a highly pure retinal pigment epithelial cell can be obtained in a short production period by a simple and easy operation. A method of concentrating retinal pigment epithelial cells is not particularly limited as long as it is generally known as a method of concentrating cells and, for example, methods such as filtration, centrifugation, perfusion separation, flow cytometry separation, trap separation by antibody immobilized carrier and the like can be used. Preferably, a method such as filtration using nylon mesh and the like can be utilized.

According to the production method of the present invention, human pluripotent stem cells can be rapidly adhered to an incubator via laminin-E8 superior in cell adhesion, and culture in an immobilized state markedly improves differentiation induction efficiency and, moreover, cell loss during medium exchange can be suppressed. Therefore, cell population of retinal pigment epithelial cells at a high concentration can be obtained in a large amount. Furthermore, cell purification can be performed by a simple and easy operation, the time necessary for a purification step can be shortened, and retinal pigment epithelial cells can be produced extremely efficiently. In addition, according to the production method of the present invention, retinal pigment epithelial cells can be adhered to each other to form a sheet-like structure. Therefore, a sheet of retinal pigment epithelial cells can be produced by the production method of the present invention. The sheet of retinal pigment epithelial cells is useful as a cell population to be used as a cell transplantation therapeutic drug for the treatment of retinal diseases, as described in detail below in 3.

2. Amplification Method of Retinal Pigment Epithelial Cell

The present invention also relates to an amplification method of retinal pigment epithelial cells, comprising a step of adhesion culture of retinal pigment epithelial cells by using a culture substrate coated with laminin-E8 (hereinafter to be referred to as "the amplification method of the present invention"). According to the amplification method of the present invention, retinal pigment epithelial cells can be easily grown by a convenient method.

As the retinal pigment epithelial cell in the amplification method of the present invention, retinal pigment epithelial cells derived from a mammal can be used. Examples of the mammal include mouse, rat, guinea pig, hamster, rabbit, cat, dog, sheep, swine, bovine, horse, goat, monkey and human. Human retinal pigment epithelial cell is preferably used when retinal pigment epithelial cells are produced for the purpose of transplanting to human, and the like.

The retinal pigment epithelial cell in the amplification method of the present invention refers to epithelial cells constituting retinal pigment epithelium, and progenitor cells thereof. Examples thereof include retinal pigment epithelial cell derived from a living organism; retinal pigment epithelial cell induced to differentiate from an undifferentiated cell (pluripotent stem cell, precursor of retinal pigment epithelial cell etc.); retinal pigment epithelial cell transdifferentiated from a differentiated cell or a precursor of a cell other than retinal pigment epithelial cell etc., preferably a retinal pigment epithelial cell induced to differentiate from an undifferentiated cell, more preferably a retinal pigment epithelial cell induced to differentiate from a pluripotent stem cell, which is obtained by the above-mentioned production method of the present invention.

The concentration of the retinal pigment epithelial cells used for the amplification method of the present invention is not particularly limited as long as uniform adhesion culture of retinal pigment epithelial cells is possible. For example, when a 10 cm dish is used, it is $1\times10^5$-$1\times10^8$ cells, preferably $2\times10^6$ $5\times10^7$ cells, more preferably $5\times10^5$-$1\times10^7$ cells, per 1 dish.

The laminin-E8 fragment in the amplification method of the present invention is similar to that mentioned above, and a coating method of a culture substrate is also similar. Therefore, by culturing the retinal pigment epithelial cells obtained by the above-mentioned production method of the present invention on the same incubator coated with the laminin-E8 fragment, the obtained retinal pigment epithelial cells can be directly amplified in situ and can be obtained in large amounts. According to the amplification method of the present invention, moreover, the cells contained in the differentiation-induced retinal pigment epithelial cells, which could not be induced to differentiate can be relatively reduced. Therefore, the amplification method of the present invention can also be used as a purification method of retinal pigment epithelial cells.

As the laminin-E8 to be used in the amplification method of the present invention, particularly, laminin-511 E8 is preferable among laminin-E8, since it has binding specificity to $\alpha3\beta1$ integrin and $\alpha7\beta1$ integrin in addition to $\alpha6\beta1$ integrin, and can contribute to the stabilization of maintenance culture of retinal pigment epithelial cells and cell proliferation, by improving the adhesion activity to retinal pigment epithelial cells.

According to the amplification method of the present invention, since retinal pigment epithelial cells are rapidly fixed on an incubator via laminin-E8 superior in cell adhesiveness, cell loss during medium exchange can be suppressed, and deformation of cell form due to passage can be suppressed, the maintenance culture and culture growth of retinal pigment epithelial cells can be performed stably.

According to the amplification method of the present invention, moreover, a membranous retinal pigment epithelial cell group can also be utilized directly or after recovery by separation from the culture substrate, as a therapeutic drug for retinal diseases shown below.

3. Retinal Pigment Epithelial Cell

The retinal pigment epithelial cells obtained by the production method or amplification method of the present invention are cultured on laminin-E8, particularly laminin-511 E8. Therefore, they can be easily recovered by separation from the culture substrate singly as cells, or as a sheet, and have superior property.

4. Therapeutic Drug for Retinal Diseases

The retinal pigment epithelial cells produced by the production method of the present invention, and the retinal pigment epithelial cells amplification by the amplification method of the present invention can be used as a cell transplantation therapeutic drug to be transplanted in the form of a suspension or sheet to living organisms for the treatment of retinal diseases. Retinal disease is an ophthalmic disease relating to the retina and also includes complications with other diseases such as diabetes and the like.

5. Toxicity, Efficacy Evaluation Drug

The retinal pigment epithelial cells produced by the production method of the present invention can be utilized as a normal or disease model cell for screening for therapeutic drugs for retinal diseases and therapeutic drug for diseases of other complications such as efficacy evaluation diabetes and the like, or prophylactic drug thereof, safety test of chemical substances and the like, stress test, toxicity test, side effect test, infection/contamination test. On the other hand, they can also be utilized for toxicity study, toxicity test and the like of phototoxicity unique to retinal cells, retinal excitotoxicity and the like. The evaluation method thereof includes stimulation, toxicity tests such as apoptosis evaluation and the like, as well as tests for evaluation of influence on normal differentiation from progenitor cell into retinal pigment epithelial cell and visual cell (expressed protein analysis and phagocytic capacity test by RT-PCR of various gene markers, ELISA of cytokine and the like), toxicity test of phototoxicity and the like, retinal electric potential and transepithelial impedance on visual function, cell injury test caused by autoimmune reaction and the like. As a cell material for these tests, not only retinal pigment epithelial cells but also progenitor cells thereof can be used and, for example, a plate on which cells are adhered by seeding, a cell suspension, a sheet or compact thereof can be provided. They can be used as an extrapolation test of human and animal tests.

The contents disclosed in any publication cited in the present specification, including patents and patent applications, are hereby incorporated in their entireties by reference, to the extent that they have been disclosed herein.

The present invention is explained in more detail in the following by referring to Examples, which are not to be construed as limitative.

EXAMPLES

Example 1 Production of RPE Cell Derived from iPS Cell

Reagents differentiation induction basic medium (GMEM medium (Invitrogen), KSR (Invitrogen), 0.1 mM MEM non-essential amino acid solution (Invitrogen), 1 mM pyruvic acid sodium (SIGMA), 0.1 M 2-mercaptoethanol (Wako Pure Chemical Industries, Ltd.), 100 U/ml penicillin-100 μg/ml streptomycin (Invitrogen))

primary differentiation induction medium (differentiation induction basic medium containing 20% KSR, 10 UM Y-27632 (Wako Pure Chemical Industries, Ltd.), 5 μM SB431542 (SIGMA), 3 μM CKI-7 (SIGMA))

secondary differentiation induction medium (differentiation induction basic medium containing 15% KSR, 10 UM Y-27632 (Wako Pure Chemical Industries, Ltd.), 5 μM SB431542 (SIGMA), 3 μM CKI-7 (SIGMA))

tertiary differentiation induction medium (differentiation induction basic medium containing 10% KSR, 10 μM Y-27632 (Wako Pure Chemical Industries, Ltd.), 5 μM SB431542 (SIGMA), 3 μM CKI-7 (SIGMA))

quaternary differentiation induction medium (differentiation induction basic medium containing 10% KSR)·

RPE maintenance medium (67% DMEM low glucose (SIGMA), 29% F12 (SIGMA), 1.9 mM L-glutamine (Invitrogen), 1.9% B-27 supplement (Invitrogen), 96 U/mL penicillin sodium, 96 μg/mL streptomycin sulfate)

Production of Retinal Pigment Epithelial Cell (Differentiation Induction)

iPS cells (1120C7, provided by Kyoto University) derived from human peripheral blood (mononuclear cell) were seeded in a laminin-coated culture dish (manufactured by Sumitomo Bakelite Co., Ltd.) at $9 \times 10^6$ cells/9 cm dish. The laminin-coated culture dish was produced by coating a 9 cm culture dish (BD FALCON) with a 0.5 μg/cm$^2$ aqueous solution of laminin-511 E8 fragment (protein disclosed in Example (3) of WO 2011043405. (manufactured by Nippi (iMatrix-511, NIP-8920-02))) at 37° C. for not less than 1 hr. iPS cells rapidly adhered on the culture dish, and formation of floating aggregate was not confirmed.

The above-mentioned differentiation induction was performed according to the following timeline, and differentiation induction in the Examples and Comparative Examples in the present specification followed this timeline. With the first day of culture as Day 0, the total amount of the medium was exchanged every day from the start of the culture (Day 1) to around Day 40 when pigment cell was confirmed. The composition of the medium was changed in stages as shown below. That is, the primary differentiation induction medium (20% KSR) was used for Day 1-4, the secondary differentiation induction medium (15% KSR) was used for Day 5-8, the tertiary differentiation induction medium (10% KSR) was used for Day 9-12, and the quaternary differentiation induction medium (10% KSR) was used from Day 13 to around Day 40 when pigment cells are confirmed.

After around Day 40 when pigment cells were confirmed, the total amount of the medium was exchanged with RPE maintenance medium up to Day 47 at not less than once per 3 days. As the culture proceeded, the cell pigment became darker, and on Day 47, many cell groups containing dark pigments were observed. On Day 47, a cell population containing pigment cells was recovered.

Using laminin-511 E8 fragment as a coating agent, seeded iPS cells rapidly adhered to the culture dish at a high density, and stably maintained an adhesion state even during culture period in a differentiation induction medium. Therefore, the cell loss could be suppressed low even when the total populations of Example 1 and Example 2. The purity (n=4) of the obtained cell populations was 96.4%, 100%, 98.6% or 99.6%.

As one example, the purity calculation data of a dish with 98.6% purity is shown.

TABLE 1

| | | | | | | | | |
|---|---|---|---|---|---|---|---|---|
| purity calculation data of RPE cell with 98.6% purity | | | | | | | | |
| | positive cell | | | | negative | | | |
| | | pigment negativity | | | cell | | | |
| visual field | pigment positive | Bestrophin positive | Pax6 positive | Bestrophin, Pax6 both positive | Bestrophin, Pax6 both negative | total positive cells | total cells | purity (%) |
| 1 | 11 | 0 | 0 | 6 | 0 | 17 | 17 | 98.6 |
| 2 | 176 | 5 | 33 | 30 | 4 | 244 | 248 | |
| 3 | 88 | 0 | 0 | 14 | 1 | 102 | 103 | | amount of medium was repeatedly exchanged. Furthermore, the rate of generation of pigment cells was drastically improved and the differentiation induction efficiency was markedly improved as compared to when the iPS cells were seeded on an incubator coated with collagen.

Example 2 Production of RPE Cell (Other iPS Cell)

By a method similar to that of Example 1 except that iPS cells (201B7, provide by Kyoto University) derived from human skin (fibroblast) were used instead of iPS cells (1120C7, provide by Kyoto University) derived from human peripheral blood (mononuclear cell) were used, pigment cells were obtained.

As a result, like Example 1, the rate of generation of pigment cells relative to the seeded iPS cells was drastically improved and the differentiation induction efficiency was markedly improved.

Example 3 Amplification of RPE Cell Derived from iPS Cell

The cell population containing pigment cells on Day 47, which underwent adhesion culture in the culture dish in Example 1 and Example 2, was treated with 0.01% Trypsin-0.53 mM EDTA and cell aggregates were detached from the culture dish. Then, adhesion between the cells was detached by mild pipetting. Protease liquid and residual impurities thereof in the cell mixture were removed together with the supernatant by centrifugation, then, unnecessary cells were separated by filtration separation through a cell strainer (DB Falcon Cell Strainer 40 µm Nylon), and a cell population containing RPE cells was recovered (Day 48).

The obtained cells were seeded in RPE maintenance medium described in Example 1 in the same 5 culture dishes coated with laminin-511 E8 as in Example 1 at 9×10⁶ cells/9 cm dish, and standing culture was performed until around Day 50 when adhesion of the RPE cell colony was confirmed.

From Day 51 to Day 71, the total amount of the medium was exchanged with RPE maintenance medium not less than once in 3 days for 3 weeks, then subjected to filtration separation using a filter, seeded in each of the same 5 culture dishes coated with laminin-511 E8, and similarly cultured for 2 weeks. As a result, retinal pigment epithelial cells were amplified to the yield of 25 dishes (10 cm dish) from any cell As for purity, immunostaining for Pax6 and Bestrphin was performed, and when either was stained, the cell was judged to be an RPE cell. When fluorescence was not observed, the presence or absence of intracellular melanin pigment was examined, and the cell was judged to be an RPE cell based on the confirmation of the pigment (since some pigments inhibit fluorescence observation, cell was judged to be RPE cell in the presence of pigment even when fluorescence was not observed). The purity was determined by a method including adding each as positive cells.

This Example afforded similar results even when iPS cells of a different line (201B7) were used.

Comparative Example 1

By a method similar to that of Example 1 except that, in the differentiation induction step of Example 1, floating culture was performed using a non-adhesive culture dish (Nunc) treated with MPC (2-methacryloxylethyl phosphoryl choline) instead of adhesion culture using a culture dish coated with laminin-511 E8 (BD FALCON), a differentiation induction step was performed.

As a result, almost all pigment cells were lost during medium exchange in the differentiation induction step, pigment cell could not be recovered on Day 47.

Comparative Example 2

By a method similar to that in Example 1 except that, in the differentiation induction step of Example 1, adhesion culture was performed using a culture dish coated with poly-D lysine and gelatin instead of a culture dish coated with laminin-511 E8, differentiation induction was performed.

The adhesiveness of the cell to the poly-D lysine/gelatin-coated culture dish was weak as compared to the laminin-511 E8-coated culture dish, and the cells were easily lost during medium exchange. Therefore, the rate of the pigment cells on Day 47 after the start of the culture was not more than ¹⁄₂₀ of Example 1 by visual observation of the number of pigment cells relative to the total cells in the culture dish, and differentiation induction efficiency was also markedly low.

(Evaluation 1) Expression of RPE Cell Marker

The pigment cells obtained in Examples 1-3 were subjected to RT-PCR analysis using primers having the following sequences, according to the method described in Journal of Cell Science 2009 Sep. 1 122 3169-79. As a result, expression of RPE cell specific genes (RPE65, CRALBP, MERTK, BEST1) was found, similar to commercially available human RPE cell lines, thus confirming RPE cells.

RPE65-F TCC CCA ATA CAA CTG CCA CT (SEQ ID NO: 1)

RPE65-R CCT TGG CAT TCA GAA TCA GG (SEQ ID NO: 2)

CRALBP-F GAG GGT GCA AGA GAA GGA CA (SEQ ID NO: 3)

CRALBP-R TGC AGA AGC CAT TGA TTT GA (SEQ ID NO: 4)

MERTK-F TCC TTG GCC ATC AGA AAA AG (SEQ ID NO: 5)

MERTK-R CAT TTG GGT GGC TGA AGT CT (SEQ ID NO: 6)

BEST1-F TAG AAC CAT CAG CGC CGT C (SEQ ID NO: 7)

BEST1-R TGA GTG TAG TGT GTA TGT TGG (SEQ ID NO: 8)

Figure 2:
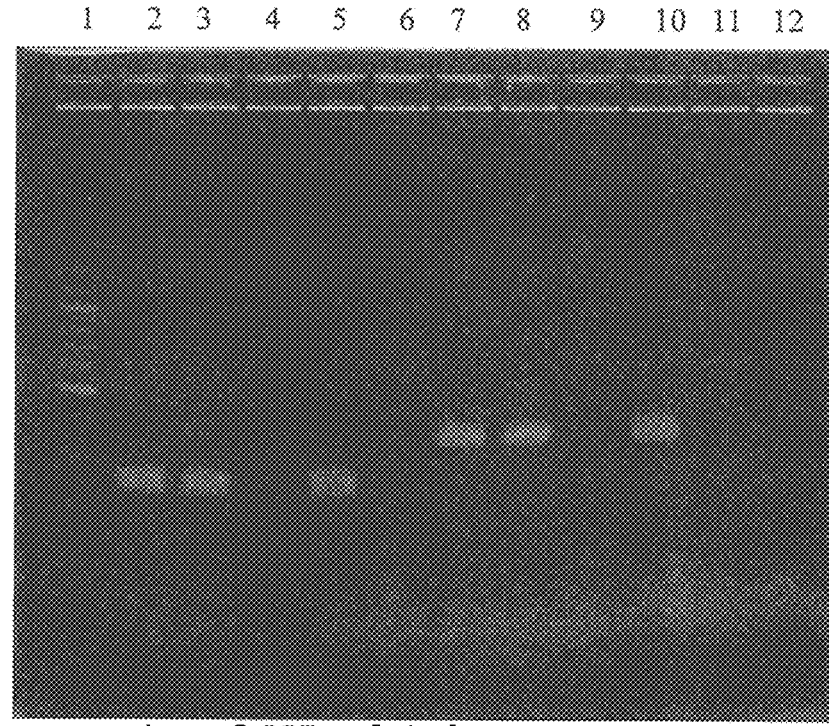
FIG. 2 shows expression of RPE-related genes by RPE cells induced from human iPS cells (201B7).

This Example afforded similar results even when iPS cells of a different line (201B7) were used. As a representative Example, the results obtained using RPE65 are shown in FIG. 2.

(Evaluation 2) Cytokine Secretional Capacity

The pigment cells obtained in Examples 1-3 were detected for the production amount of PEDF by ELISA according to the method described in IOVS. 2006 47 612-3624. As a result, it was confirmed that they similarly had cytokine secretional capacity like the RPE cells of adult retina (Table 2).

TABLE 2

| | PEDF secretion amount | | | | |
|---|---|---|---|---|---|
| days | concentration (ng/mL) | | | | |
| after passage | Example 1 | Example 2 | Example 3 | mean | standard error |
| 7 | 945.2 | 998.8 | 993.3 | 979.1 | 17.0 |
| 10 | 1266.1 | 1263.1 | 1288.0 | 1272.4 | 7.9 |
| 12 | 1574.3 | 1567.0 | 1616.3 | 1585.8 | 15.4 |
| 14 | 1542.0 | 1622.4 | 1524.3 | 1562.9 | 30.2 |
| 17 | 1621.2 | 1533.5 | 1482.9 | 1545.8 | 40.4 |
| 19 | 1727.7 | 1752.7 | 1842.8 | 1774.4 | 35.0 |
| 21 | 1504.8 | 1581.0 | 1570.6 | 1552.1 | 23.8 |

This Example afforded similar results even when iPS cells of a different line (201B7) were used.

(Evaluation 3) Phagocytic Capacity

The pigment cells obtained in Examples 1-3 were analyzed for the phagocytic capacity according to the method described in J Cell Sci. 1993 104 37-49, and using FLUO-SPHERES (registered trade mark) fluorescence microsphere (Invitrogen, F13081). As a result, it was confirmed that the cells had phagocytic capacity of the same level as commercially available human RPE cell line. This Example afforded similar results even when iPS cells of a different line (201B7) were used. In addition, similar results were obtained even when the phagocytic capacity was analyzed using iPS cells of a different line (201B7) and PHROD GREEN E. COLI BIOPARTICLES (registered trade mark)

Conjugate for Phagocytosisb (Molecular Probes, P35366), according to the method described in The Lancet 2012 379 713-720.

Comparative Example 3

By a method similar to that in Example 1 and using iPS cells (201B7, provided by Kyoto University) derived from human skin (fibroblast) in the same manner as in Example 2 and a culture dish coated with any of the following 1)-3), differentiation induction was performed. A test including simultaneously subjecting 3 substrates to differentiation induction was performed twice, and a supplemental test was performed once for each substrate.

1) Laminin-511 E8 (molecular weight 150,000) (iMa-trix511: manufactured by Nippi, NIP-8920-02) was used for coating at 0.5 µg/cm$^2$.
2) Human recombinant laminin-511 full-length (molecular weight 776,000) (sold by: VERITAS Corporation (produced by: BioLamina)/BLA-LN511) was used for coating at 2.59 µg/cm$^2$.
3) MATRIGEL (manufactured by BD, 354230 (total protein concentration: 9-12 mg/ml)) (basal lamina matrix, soluble basal lamina preparation derived from mouse Engelbreth-Holm-Swarm (EHS) sarcoma, containing major molecules of basal lamina, type IV collagen, nidogen, perlecan, laminin-111) is dissolved overnight at 4° C., and used in the cold state for coating a culture container at 10 mL/57 cm$^2$ (0.175 ml/cm$^2$).

Figure 3:
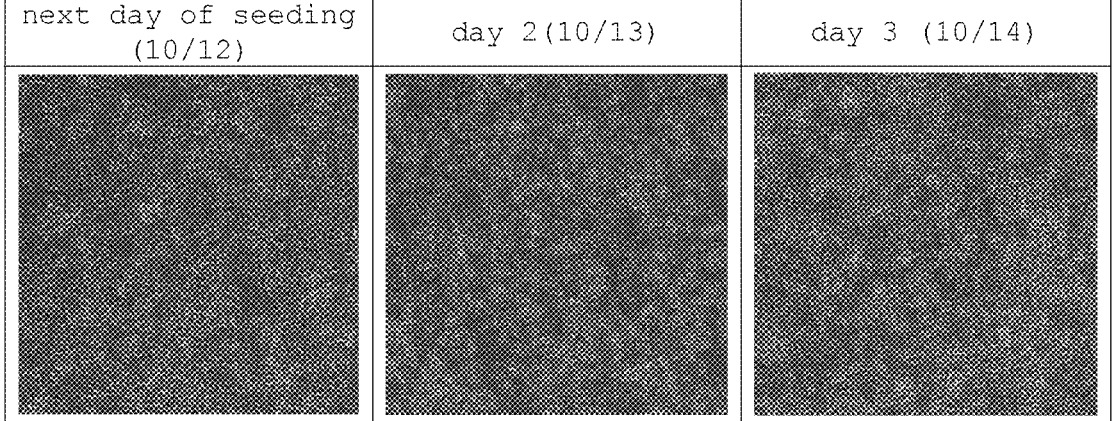
FIG. 3 shows the cell adhesion state on days 1, 2 and 3 after the start of differentiation induction of iPS cells seeded on a substrate coated with laminin-511 E8, MATRIGEL or laminin-511 full-length in Comparative Example 3.
Figure 3:
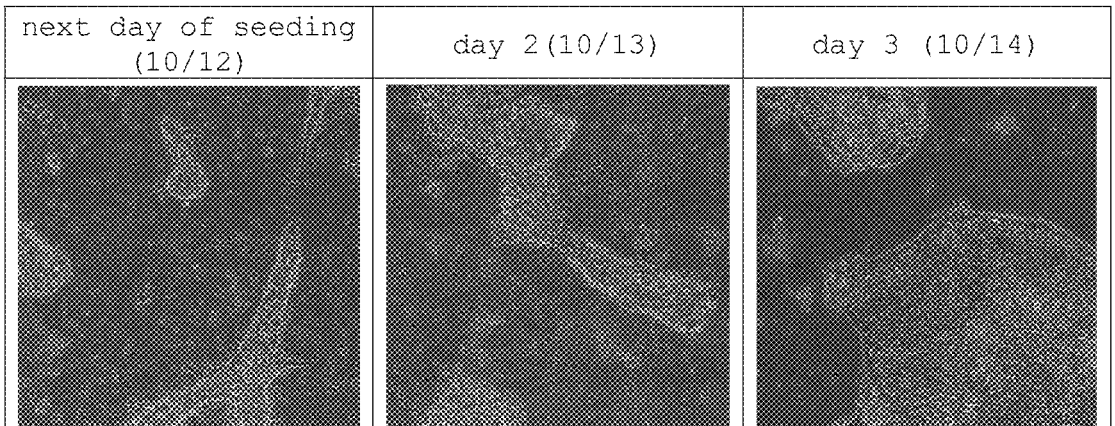
Figure 3:
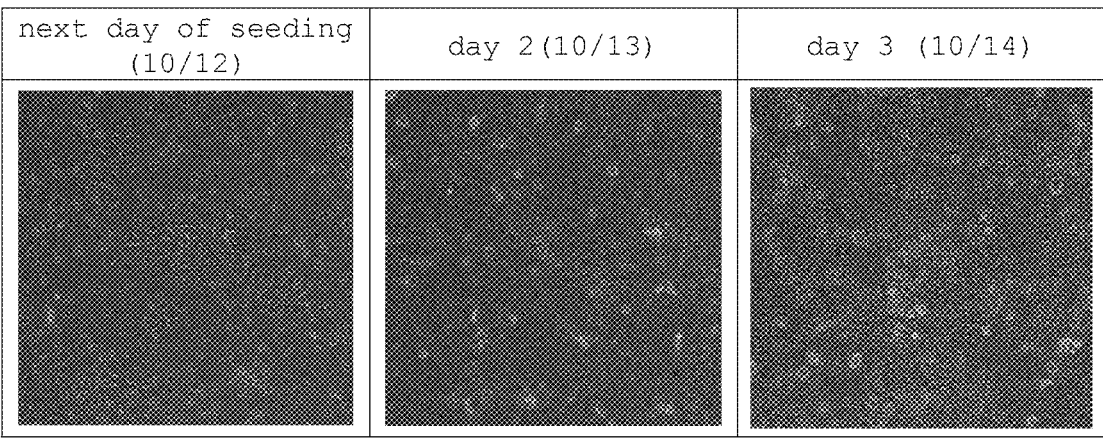

The state of cell adhesion on day 1, day 2 and day 3 from the start of differentiation induction is shown in FIG. 3. In the case of a laminin-511 E8-coated substrate, from the next day of seeding, the cells grew while uniformly adhering to the whole surface of the dish, and rapidly entered the differentiation induction process. In the case of a MATRI-GEL (laminin-111)-coated substrate, cell adhesion was inconsistent, with a part invading into the gel, and eventually failed to form a whole surface layer. In the case of a laminin full-length-coated substrate, adhesion was weak and the cells partly formed a colony on the next day of seeding. It took 4-5 days for the cells to grow and spread over the entire surface of the dish. Therefore, the differentiation induction process became uneven to leave a part where differentiation induction did not proceed.

Figure 4:
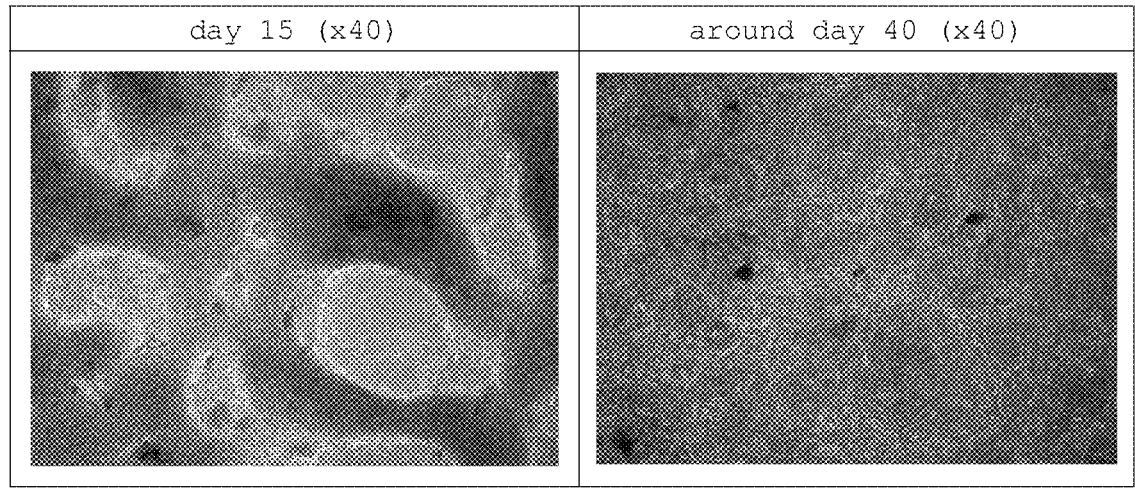
FIG. 4 shows cell populations on days 15 and 40 after the start of differentiation induction of iPS cells seeded on a substrate coated with laminin-511 E8, MATRIGEL or laminin-511 full-length in Comparative Example 3.
Figure 4:
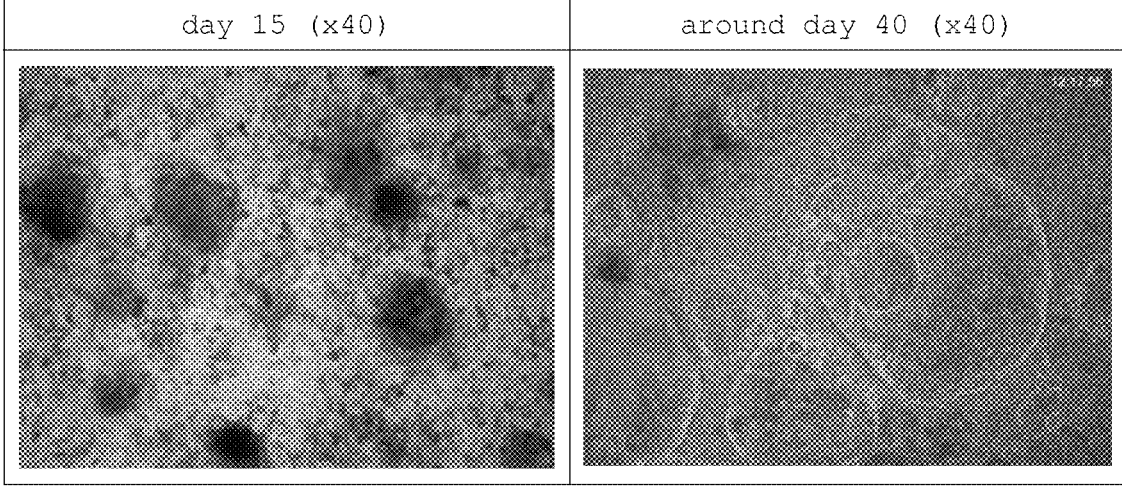
Figure 4:
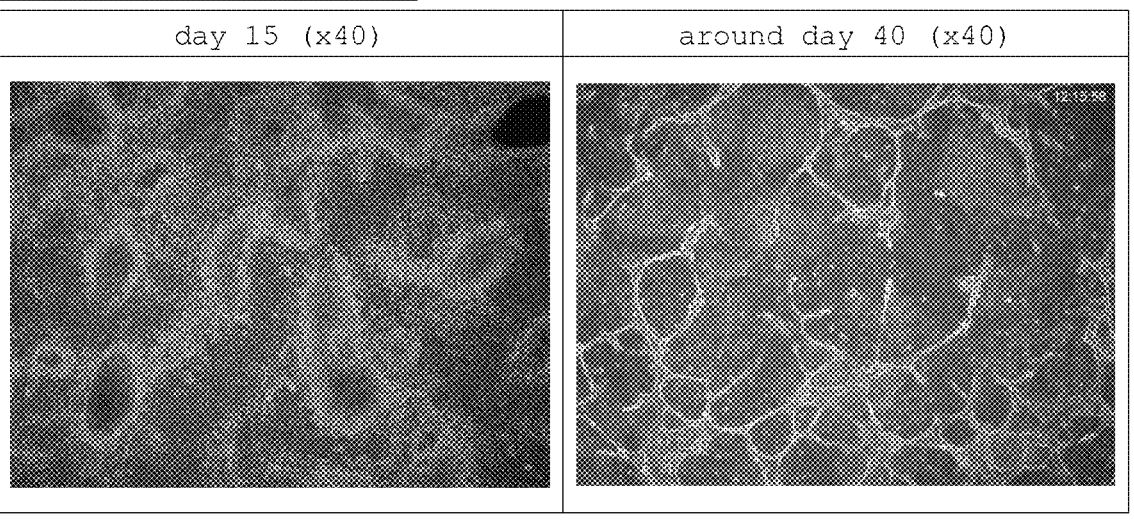

The state of cell population on day 15 from the start of differentiation induction and before the filtration separation step of the cells (around day 40) is shown in FIG. 4. In the case of a laminin-511 E8-coated substrate, cells were spread on the entire surface around day 15, layered cells were accumulated thick, and melanin color development was observed. Around day 40, cells were layered uniformly and thick, and breakage or delamination of the basement was not found. Clear melanin-containing cell aggregates were found on the top part of the multilayer. In the case of a MATRI-GEL-coated substrate, a uniform layer of adherent cells was not found around day 15, and the cells were drawn into the inside of the gel. Around day 40, a clear cellular membrane in a single layer was not formed on the basement side, and melanin color development was not observed. In the case of a laminin full-length-coated substrate, around day 15, adherent cells were observed on the whole surface, but differentiation induction did not proceed in many parts, and breakage or delamination of the adhesion surface layer was sometimes found in other lots. In addition, poorly-layered cells were found on the upper part, and melanin color development was extremely weak. The layered cells gradually fell off from around day 20, and the cellular membrane on the basement side was remarkably broken around day 40.

From the above, growth failure and differentiation induction failure were observed in the case of a MATRIGEL-coated substrate, and a decrease in the adherent cell number and vulnerability in the number of layered cells were remarkably shown, efficiency of RPE cell appearance shown by melanin color development, and differentiation induction rate thereof were markedly low, and the yield of finally-obtained RPE cells was low in the case of a laminin full-length-coated substrate. Therefore, it was clarified that a culture substrate coated with laminin-E8 fragment in the present invention can produce retinal pigment epithelial cells extremely efficiently.

INDUSTRIAL APPLICABILITY

According to the production method of the present invention, retinal pigment epithelial cells can be produced efficiently by a simple and easy method using a culture substrate coated with laminin-E8 fragment. The production method of the present invention is superior in the differentiation induction efficiency and can purify retinal pigment epithelial cells by a simple and easy operation, and can produce retinal pigment epithelial cells in a high yield by suppressing cell loss during the step. The retinal pigment epithelial cells produced by the method of the present invention are useful not only for the treatment of retinal diseases but also as normal and disease model cells.

This application is based on a patent application No. 2013-212345 filed in Japan (filing date: Oct. 9, 2013), the contents of which are incorporated in full herein.

---

The invention claimed is:

1. A production method of retinal pigment epithelial cells, consisting of the steps of (i) adherent culturing human pluripotent stem cells on a culture substrate coated with a laminin-511E8 fragment, (ii) culturing the cells obtained in step (i) on a culture substrate coated with a laminin-511E8 fragment and in a medium containing 20% knockout serum replacement (KSR) for 4 days;

(iii) culturing the cells obtained in step (ii) on a culture substrate coated with a laminin-511E8 fragment and in a medium containing 15% KSR for 4 days;

(iv) culturing the cells obtained in step (iii) on a culture substrate coated with a laminin-511E8 fragment and in a medium containing 10% KSR, and (v) recovering the retinal pigment epithelial cells by treating the cells obtained in step (iv) with a protease solution.

2. The method according to claim 1, wherein the culturing of steps (ii), (iii), and (iv) is performed in the presence of a differentiation-inducing factor.

3. The method according to claim 1, wherein the human pluripotent stem cells are human iPS cells.

4. The method according to claim 2, wherein the human pluripotent stem cells are human iPS cells.

5. An amplification method of retinal pigment epithelial cells, consisting of the steps of (i) adherent culturing human pluripotent stem cells on a culture substrate coated with a laminin-511E8 fragment, (ii) culturing the cells obtained in step (i) on a culture substrate coated with a laminin-511E8 fragment and in a medium containing 20% knockout serum replacement (KSR) for 4 days;

(iii) culturing the cells obtained in step (ii) on a culture substrate coated with a laminin-511E8 fragment and in a medium containing 15% KSR for 4 days;

(iv) culturing the cells obtained in step (iii) on a culture substrate coated with a laminin-511E8 fragment and in a medium containing 10% KSR, and (v) recovering the retinal pigment epithelial cells by treating the cells obtained in step (iv) with a protease solution.

6. The method according to claim 5, wherein the culturing of steps (ii), (iii), and (iv) is performed in the presence of a differentiation-inducing factor.

7. The method according to claim 6, wherein the human pluripotent stem cells are human iPS cells.

8. The method according to claim 5, wherein the human pluripotent stem cells are human iPS cells.

9. A purification method of retinal pigment epithelial cells, consisting of the steps of (i) adherent culturing human pluripotent stem cells on a culture substrate coated with a laminin-511E8 fragment, (ii) culturing the cells obtained in step (i) on a culture substrate coated with a laminin-511E8 fragment and in a medium containing 20% knockout serum replacement (KSR) for 4 days;

(iii) culturing the cells obtained in step (ii) on a culture substrate coated with a laminin-511E8 fragment and in a medium containing 15% KSR for 4 days;

(iv) culturing the cells obtained in step (iii) on a culture substrate coated with a laminin-511E8 fragment and in a medium containing 10% KSR, and (v) recovering the retinal pigment epithelial cells by treating the cells obtained in step (iv) with a protease solution.

10. The method according to claim 9, wherein the culturing of steps (ii), (iii), and (iv) is performed in the presence of a differentiation-inducing factor.

11. The method according to claim 10, wherein the human pluripotent stem cells are human iPS cells.

12. The method according to claim 9, wherein the human pluripotent stem cells are human iPS cells.

* * * * *